United States Patent [19]
Rhodes

[11] Patent Number: 5,843,160
[45] Date of Patent: Dec. 1, 1998

[54] PROSTHESES FOR ANEURYSMAL AND/OR OCCLUSIVE DISEASE AT A BIFURCATION IN A VESSEL, DUCT, OR LUMEN

[76] Inventor: Valentine J. Rhodes, 608 Winding River Rd., Bricktown, N.J. 08723

[21] Appl. No.: 625,121

[22] Filed: Apr. 1, 1996

[51] Int. Cl.[6] .............................. A61F 2/06; A61M 29/02
[52] U.S. Cl. ................................ 623/1; 623/12; 606/194
[58] Field of Search ......................... 623/1, 12; 606/194, 606/195; 600/36

[56] References Cited

U.S. PATENT DOCUMENTS

| | | |
|---|---|---|
| 3,657,744 | 4/1972 | Ersek . |
| 4,047,252 | 9/1977 | Liebig et al. . |
| 4,503,569 | 3/1985 | Dotter . |
| 4,512,338 | 4/1985 | Balko et al. . |
| 4,562,596 | 1/1986 | Kornberg ..................................... 623/1 |
| 4,580,568 | 4/1986 | Gianturco . |
| 4,655,771 | 4/1987 | Wallsten ..................................... 623/1 |
| 4,733,665 | 3/1988 | Palmaz ........................................ 623/1 |
| 4,740,207 | 4/1988 | Kreamer ..................................... 623/1 |
| 4,776,337 | 10/1988 | Palmaz ........................................ 623/1 |
| 4,795,458 | 1/1989 | Regan ......................................... 623/1 |
| 4,830,003 | 5/1989 | Wolff et al. ................................. 623/1 |
| 4,856,516 | 8/1989 | Hillstead .................................... 623/1 |
| 4,994,071 | 2/1991 | MacGregor ............................. 606/194 |
| 5,035,706 | 7/1991 | Giantureo et al. ...................... 606/198 |
| 5,122,154 | 6/1992 | Rhodes ........................................ 623/1 |
| 5,207,695 | 5/1993 | Trout, III ..................................... 623/1 |
| 5,211,658 | 5/1993 | Clouse ........................................ 623/1 |
| 5,275,622 | 1/1994 | Lazarus et al. ............................. 623/1 |
| 5,282,824 | 2/1994 | Gianturco ................................... 623/1 |
| 5,316,023 | 5/1994 | Palmaz et al. .............................. 623/1 |
| 5,330,528 | 7/1994 | Lazim ......................................... 623/1 |
| 5,360,443 | 11/1994 | Barone et al. .............................. 623/1 |
| 5,370,691 | 12/1994 | Samson ..................................... 623/12 |
| 5,387,235 | 2/1995 | Chuter ........................................ 623/1 |
| 5,405,379 | 4/1995 | Lane ........................................... 623/1 |
| 5,562,724 | 10/1996 | Vorwerk et al. .......................... 623/12 |
| 5,632,772 | 5/1997 | Alcime et al. ............................. 623/12 |
| 5,665,117 | 9/1997 | Rhodes ..................................... 623/12 |

*Primary Examiner*—Randy C. Shay
*Attorney, Agent, or Firm*—Caesar, Rivise, Bernstein, Cohen & Pokotilow, Ltd.

[57] ABSTRACT

Expandable intraluminal prostheses for the treatment of aneurysmal disease or occlusive disease at a bifurcation of a vessel, duct, or lumen, e.g, disease at the aorto-iliac bifurcation. Each prosthesis includes three expandable, sleeve sections which are arranged to be located in respective portions of the vessel, duct, or lumen contiguous with the bifurcation, and secured together in situ. The prosthesis for aorto-iliac aneurysmal disease includes a common, stent-supported sleeve section having an expandable outer balloon for engaging and trapping the thrombus in the aneurysmal space in the abdominal aorta, and a pair of stent-supported sleeve limb sections. The limb sections are connected to the common section to provide a passage for blood to flow through the prosthesis. One or more of the limb sections can also include a outer balloon for engaging the thrombus within its associated aneurysmal space. Sealing mesh is provided on the prosthesis to prevent the egress of emboli and to permanently secure it in place. The prosthesis for aorto-iliac occlusive disease is similar the prothesis for aneurysmal disease, except that the sections of the prosthesis do not include an outer balloon.

13 Claims, 8 Drawing Sheets

PROSTHESES FOR ANEURYSMAL AND/OR OCCLUSIVE DISEASE AT A BIFURCATION IN A VESSEL, DUCT, OR LUMEN

BACKGROUND OF THE INVENTION

The invention relates generally to medical devices for use in vessels, ducts or lumens of living beings, and more particularly to expandable prostheses for the treatment of aneurysmal and/or aorto-iliac occlusive disease.

Various prior art publications have disclosed prostheses for treating occlusive arterial disease. In particular, examples of various types of expandable grafts/stents are disclosed in U.S. Pat. Nos. 3,657,744 (Ersek), 4,047,252 (Liebig et al), 4,503,569 (Dotter), 4,512,338 (Balko et al.) 4,580,568 (Gianturco), 4,655,771 (Wallsten), 4,733,665 (Palmaz), 4,740,207 (Kreamer), 4,776,337 (Palmaz), 4,795,458 (Regan), 4,830,003 (Wolff et al.), 4,856,516 (Hillstead), 4,994,071 (MacGregor), and 5,035,706 (Gianatureo et al.) and in the following literature: "Balloon-Expandable Intra-coronary Stents in the Adult Dog", Circulation, August 1987, pages 450–456, Vol. 76, No. 2; "Normal and Stenotic Renal Arteries: Experimental Balloon-expandable Intraluminal Stenting", Radiology, 1987, pages 705–708, Vol. 164, No. 3; "A Titanium-Nickel Alloy Intravascular Endoprosthesis", Transactions American Society of Artificial Internal Organs, 1988, pages 399–403, Vol. XXXIV; "Self-Expanding Endovascular Stent in Experimental Atherosclerosis", Radiology, March 1989, pages 773–778, Vol. 170, No. 3; "Emergency Stenting for Acute Occlusion After Coronary Balloon Angioplasty", Circulation, November 1988, pages 1121–1127, Vol. 78, No. 5; "Intravascular Stents for Angioplasty", CARDIO, December 1987; "Intra-Arterial Stenting in the Atherosclerotic Rabbit", Circulation, September 1988, pages 646–653, Vol. 78, No. 3; "Intravascular Stents to Prevent Occlusion and Restenosis After Transluminal Angioplasty", The New England Journal of Medicine, March 1987, pages 701–706, Vol. 316, No. 12; "A Polyester Intravascular Stent for Maintaining Luminal Patency", Texas Heart Institute Journal, Nov. 1, 1988, pages 12–16, Vol. 15. "Post Dilatation Stenting; Early Experience of the Use of an Endocoronary Prosthesis to Prevent Restenosis Recurrance After Angioplasty", J. Cardiovasc. Surg. 28, 1987, Session 8: CARDIAC-CORONARY (II); "Intravascular Stents to Prevent Occlusion and Restenosis After Transluminal Angioplasty", Abstract from New England Journal of Medicine 1987, Volume 316, pages 701–706; "Vascular Stenting in Normal and Atherosclerotic Rabbits", Circulation, February 1990, Vol. 81, No. 2, pages 667–683; Treatment of Major Venous Obstruction with an Expandable Endoluminal Spiral Prosthesis, J. Cardiovasc. Surg. 30, 1989, pages 112–117; and Venous Stenases in Dialysis Shunts: Treatment with Self-Expanding Metallic Stents, Radiology, February 1989, Vol. 170, No. 2, pages 401–405.

While the foregoing prior art may have been generally suitable for its intended purposes it still appears to have left much to be desired from various standpoints.

In my U.S. Pat. No. 5,122,154, whose disclosure is incorporated by reference herein, there is disclosed a prosthesis in the form of an intraluminal graft for use in a vessel, duct, or lumen which overcomes many of the disadvantages of the prior art and which has particular application for treating occlusive arterial disease. For such an application the intraluminal graft is arranged to be placed in an artery having a narrowing or stenotic lesion to hold increase the patency thereof. The graft comprises a sleeve having plural stents thereon. The sleeve is an elongated tubular member formed of a conventional graft material which is flexible and impervious to the ingrowth of tissue therein. Each stent is a generally ring-like member formed a plurality of interconnected movable links and is mounted about the periphery of a surface, e.g., inner or outer, of the sleeve at selected points along the sleeve to form respective spaced first sleeve sections. Each of the first sections extends for only a portion of the length of the graft, thereby leaving a plurality of second sleeve sections interposed between the first sleeve sections. The stents and the sleeve are arranged to be expanded, e.g., by a balloon catheter, from a compact state to an expanded state to increase the inner cross sectional area diameter of the sleeve. In the expanded state the stents are resistant to contraction back to the compact state. The graft is able to bend with respect to its longitudinal axis to enable it to be readily accommodated within a curved artery.

While the prosthesis of my aforementioned patent is suitable for its intended purposes, it is of somewhat limited utility for treating occlusive disease at the situs of an arterial bifurcation, i.e., a narrowing or stenotic lesion in the upstream artery and in each of the downstream limbs. One such common occurrence of this type of occlusive disease is in the abdominal aorta and in the common iliac arteries adjacent the aorto-iliac bifurcation.

None of the prior art as identified above appears to adequately address the need for a viable prosthesis to treat occlusive disease at the situs of an arterial bifurcation. Thus, a need exists for such a prosthesis.

Various United States Letters patents have disclosed devices for the treatment of aneurysmal arterial disease, namely, U.S. Pat. Nos. 4,562,596 (Kornberg), 5,207,695 (Trout III), 5,211,658 (Clouse), 5,275,622 (Lazarus et al.), 5,282,824 (Gianturco), 5,316,023 (Palmaz et al.), 5,330,528 (Lazim), 5,360,443 (Barone et al.), 5,370,691 (Samson), 5,387,235 (Chuter), and 5,405,379 (Lane). While the prostheses of those patent may be generally suitable for their intended purposes they still appear to leave much to be desired from various standpoints.

In my copending U.S. patent application Ser. No. 08/562,728 filed on Nov. 27, 1995, entitled Endovascular Prosthesis For Aneurysmal Arterial Disease And Method Of Use, whose disclosure is incorporated by reference herein, there are disclosed various endovascular prosthesis for treating aneurysmal disease in a vessel, duct, or lumen which overcomes many of the disadvantages of the prior art and which is of particular utility in the abdominal aorta.

The prostheses disclosed in that application basically comprises an expandable sleeve, an outer balloon, a pair of expandable anchoring stents, plural expandable support stents, and a pair of sealing rings, e.g., loosely organized mesh rings. The sleeve is an elongated tubular member defining a passageway having a pair of open ends for conveying blood therethrough. The outer balloon is disposed about the sleeve and is arranged to be filled with a fluid, e.g., a gel or saline, to cause it to extend outward to fill the aneurysmal space, e.g., the space between the inner wall of the abdominal aorta at which the aneurysm is located and the outer surface of the balloon. The sleeve is arranged to be expanded and held in that state by the stents. The anchoring stents fixedly secure the prosthesis to the interior of the artery. The ends of the sleeve are sealed to the interior of the aorta on opposite sides of the aneurysm by the sealing rings. The sealing of the prosthesis to portions of the artery on respective sides of the aneurysm precludes the ingress of blood between the outer balloon and the interior of the artery at the aneurysm, while the blood is conveyed through the passageway, and to preclude the egress of material, e.g., an embolus, from between the outer balloon and the interior of the artery at the situs of the aneurysm.

In my U.S. Pat. No. 5,665,117 entitled Endovascular Prosthesis With Improved Sealing Means For Aneurysmal Arterial Disease And Method Of Use, which is a Continuation-In-Part of my aforementioned copending patent application Ser. No. 08/562,728 there are disclosed additional embodiments of the prosthesis of that application. The additional embodiments of those prostheses utilize a sealing covering in lieu of the pair of sealing rings to hold the prosthesis in place and to prevent the ingress of blood into the aneurysmal space. The sealing covering is a mesh like material, e.g., either a loosely organized mesh of thrombogenic, fibrogenic fibers, and extends over substantially the entire outer surface of the outer balloon. Thus, when this prosthesis is disposed within the aneurysm in the abdominal aorta and fully expanded to its operative state the covering engages the inner surface of the artery wall adjacent each end of the prosthesis to seal it (thereby achieving the function of the sealing rings of the embodiments in application Ser. No. 08/562,728), while the fibrillar fibers of the covering are compacted into the aneurysmal aortic thrombus to intermingle with the thrombus and thereby further lock and seal the prosthesis in place. Moreover, the fibrillar fibers of the covering mesh tend to seal the junctures of the abdominal aorta to the origins of its collateral branch arteries, e.g., the inferior mesenteric artery and the lumbar arteries, so that blood cannot gain ingress into the aneurysmal space from these arteries, which action could result in aortic aneurysm growth and concomitant risk of rupture. Further still, since the mesh covering is thrombogenic and fibrogenic it stimulates the incorporation of the prosthesis by fibrosis to the aortic wall, thus ensuring a complete and permanent seal. Thus, the prosthesis with the sealing covering prevents further aortic aneurysm expansion and rupture by also strengthening the aortic wall due to fibrosis.

While the prostheses of both of my aforementioned copending applications are suitable for their intended purposes, they are of somewhat limited utility for treating aneurysmal disease at the situs of a bifurcation in a vessel, duct, or lumen, i.e., an aneurysm in the upstream vessel, duct, or lumen and in each of the downstream limbs. One such common occurrence of this type of aneurysmal disease is in the abdominal aorta and in the common iliac arteries adjacent the aorto-iliac bifurcation.

Thus, a need also exists for a prosthesis for treating aneurysmal disease at a bifurcation.

OBJECTS OF THE INVENTION

It is a general object of this invention to provide prostheses which address those needs.

It is a further object of this invention to provide an expandable intraluminal prosthesis for the treatment of aneurysmal disease at a bifurcation of a vessel, duct, or lumen, e.g, aneurysmal disease at the aorto-iliac bifurcation.

It is a further object of this invention to provide an expandable intraluminal prosthesis for treating aneurysmal disease at a bifurcation of a vessel, duct, or lumen, and which is easy to place and use.

It is a further object of this invention to provide an expandable intraluminal prosthesis for the treatment of occlusive disease at a bifurcation of a vessel, duct, or lumen, e.g, occlusive disease at the aorto-iliac bifurcation.

It is a further object of this invention to provide an expandable intraluminal prosthesis for treating occlusive disease at a bifurcation of a vessel, duct, or lumen and which is easy to place and use.

SUMMARY OF THE INVENTION

These and other objects of this invention are achieved by providing prostheses and methods of use for the treatment of aneurysmal and occlusive disease in a vessel, duct, or lumen of a living being.

In an embodiment of the invention for aneurysmal disease the prosthesis is arranged so that one portion is located in the abdominal aorta of a living being at the site of an aneurysm, while other portions of the prosthesis are located within the iliac arteries at the bifurcation with the abdominal aorta. That prosthesis basically comprises central or common sleeve means, a pair of bifurcation or limb sleeves means, and outer balloon means coupled to the common sleeve means. The common sleeve means comprises an elongated tubular sleeve having an open upper end and an open lower end defining a passageway therebetween arranged to convey blood therethrough. The outer balloon means is disposed about the common sleeve and is arranged to be filled with a filling material, e.g., a gel or saline solution. Preferably, the outer balloon means is filled sufficiently to cause its outer wall to extend outward to completely fill the aneurysmal space longitudinally, but only to partially fill the aneurysmal space transversely, so that an excess force is not produced radially which could dislodge an aneurysm thrombus.

The common sleeve means is arranged to be fixedly secured to the interior of the abdominal aorta, with the upper and lower ends of it sealed to portions of the abdominal aorta on respective sides of the aneurysm to preclude the ingress of blood between the outer balloon means and the interior of the abdominal aorta, while enabling blood to be conveyed through the passageway, and to preclude the egress of material, e.g., an embolus, from between the outer balloon means and the interior of the abdominal aorta at the situs of the aneurysm.

Each of the limb sleeve means comprises an elongated tubular bifurcation sleeve having an open upper end and an open lower end defining a passageway therebetween arranged to convey blood therethrough. The upper open end of each of the bifurcation sleeves is arranged to be located and fixedly secured at a joint within the open bottom end of the common sleeve, whereupon the passageway in the common sleeve is in fluid communication with the passageways in the bifurcation sleeves. Sealing means is provided between the common sleeve and the bifurcation sleeves to preclude the egress of blood from the joint. The securement of the bifurcation sleeves to the common sleeve is effected by a joint securement means. Preferably the common sleeve and the bifurcation sleeves are expandable to an expanded state when in position, and are held in the expanded state by plural stents. Some of the stents serve to anchor the prosthesis in place in the abdominal aorta.

The sealing of the ends of the common sleeve means to the interior of the abdominal aorta is accomplished by sealing means, e.g., mesh-like rings, located adjacent the ends of the central sleeve means. The anchoring of the prosthesis in position is accomplished in the preferred embodiment by use of plural projections arranged for engagement with the interior of the wall of the abdominal aorta.

Depending upon the longitudinal extent of the aneurysms in the common iliac arteries the bifurcation sleeves may each include the same type of outer balloon means as the common sleeve.

In an embodiment of the invention for occlusive disease the prosthesis is arranged so that one portion is located in a vessel, duct, or lumen, e.g., the abdominal aorta, at the site of a narrowing or stenotic deposit, while other portions of the prosthesis are located within the contiguous portions of the vessel, duct, or lumen at the bifurcation, e.g., the common iliac arteries at the bifurcation with the abdominal aorta, and which also include stenotic deposits. This embodiment is similar, yet simpler in construction than the embodiment for aneurysmal disease. To that end, this embodiment comprises a common sleeve, a pair of bifurcation or limb sleeves, sleeve connecting means, and anchoring means. The common sleeve comprises an elongated tube having an open upper end and an open lower end defining a passageway therebetween for conveying body fluid, e.g., blood, therethrough. The common sleeve is arranged to be carried into the interior of the vessel, duct, or lumen and then secured thereto by the anchoring means, and with the upper and lower ends of the common sleeve being adjacent respective sides of the narrowing. The bifurcation sleeves are arranged to be carried into location within respective ones of the branches of the bifurcation, and into a portion of the common sleeve. Each of the bifurcation sleeves comprises an elongated tube having an open upper end and an open lower end defining a passageway therebetween for conveying the fluid therethrough. The upper open ends of each of the bifurcation sleeves are arranged to be located within and then fixedly secured to the common sleeve by the sleeve securement means at a joint within the open bottom end of the central sleeve, whereupon the passageway in the central sleeve is in fluid communication with the passageways in the bifurcation sleeves.

The means for securing the bifurcation sleeves to the central or common sleeve of each of the embodiments of this invention comprises another aspect of the subject invention, and can be used with any prior art grafts, sleeves, stents, etc., to secure them together in situ at a bifurcation of a vessel, duct, or lumen in a living being.

DESCRIPTION OF THE DRAWINGS

Other objects and many attendant advantages of this invention will become readily appreciated as the same becomes better understood by reference to the following detailed description when considered in connection with the accompanying drawings wherein.

DETAILED DESCRIPTION OF THE PREFERRED EMBODIMENTS

Figure 1:
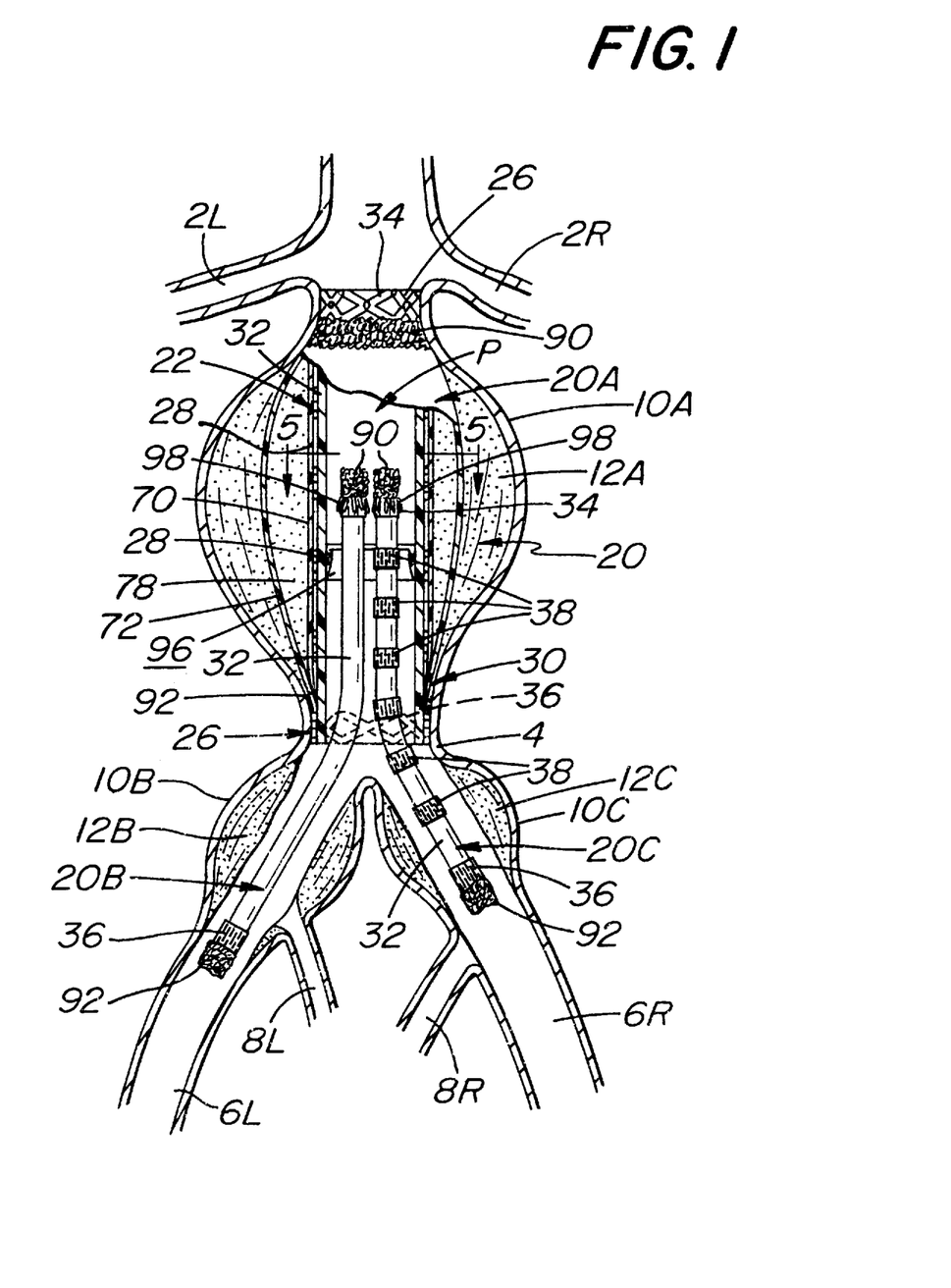
FIG. 1 is a front plan view illustration of a portion of the abdominal aorta and the common iliac arteries of a living being, each having an aneurysm therein, and showing one embodiment of a prosthesis of the subject invention configured for treating aneurysmal disease in partial section located within the aorto and common iliac arteries, the prosthesis being shown in its compact state.
Figure 10:
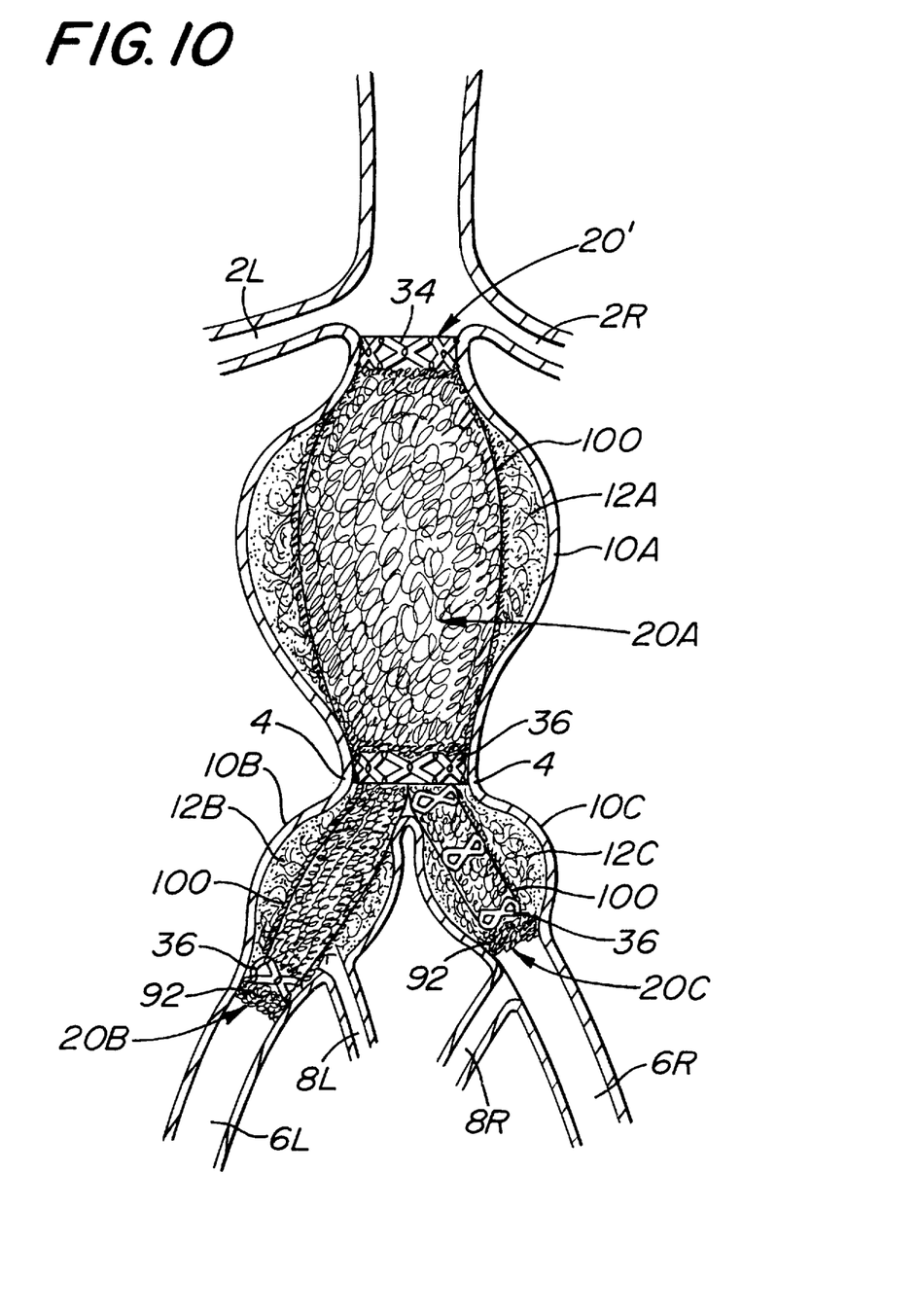
FIG. 10 is a front plan view illustration, like that of FIG. 1, showing an alternative embodiment of the prosthesis of the subject invention for use in treating aneurysmal disease shown in its expanded, fully operational state.

Referring now to various figures of the drawing where like reference numerals refer to like parts there is shown at 20 in FIG. 1 and at 20' in FIG. 10 respective embodiments of an expandable, intraluminal prosthesis constructed in accordance with this invention for treating aneurysmal disease at a bifurcation of a vessel, duct, or lumen. Moreover, there is shown at 200 in FIG. 7 one embodiment of an expandable, intraluminal prosthesis constructed in accordance with this invention for treating occlusive disease at a bifurcation of a vessel, duct, or lumen. As will be seen hereinafter all of the prostheses of this invention are composed of three, tubular, expandable components or sections which are arranged to be disposed within the bifurcated vessel, duct, or lumen, and once in position assembled in situ.

The prostheses 20 and 20' are of similar construction, except for the use of different sealing means (to be described later), and each is arranged for treating aneurysmal disease on opposite sides, i.e., upstream and downstream, of an arterial bifurcation. The most commonly anticipated application for the prostheses 20 and 20' is expected to be for treating an aneurysm in the abdominal aorta and aneurysms in the common iliac arteries adjacent the aorta-iliac bifurcation, i.e., aorto-iliac aneurysmal disease. When either prosthesis 20 or 20' is place in its operative, expanded state (to be described later) it prevents further expansion or rupture of the aneurysms, while providing for patency of the arterial path. The aorto-iliac application for the prostheses 20 and 20' is shown in FIGS. 1–6, and 10 herein.

Figure 7:
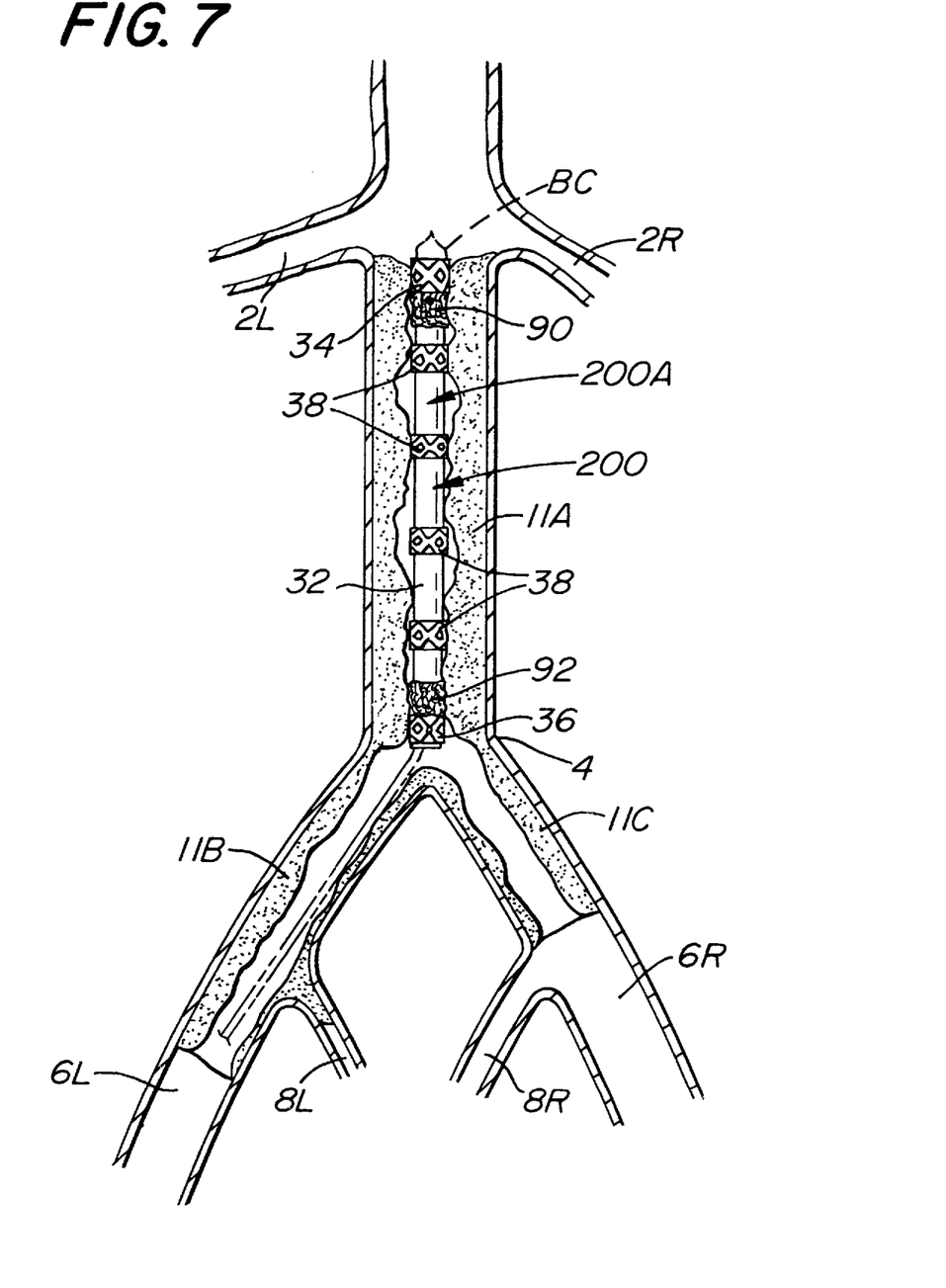
FIG. 7 is a front plan view illustration of a portion of the abdominal aorta and the common iliac arteries of a living being having occlusive vascular disease therein showing a portion of an embodiment of a prosthesis of the subject invention for use in treating occlusive disease, with the portion of the prosthesis being shown in its compact state.
Figure 8:
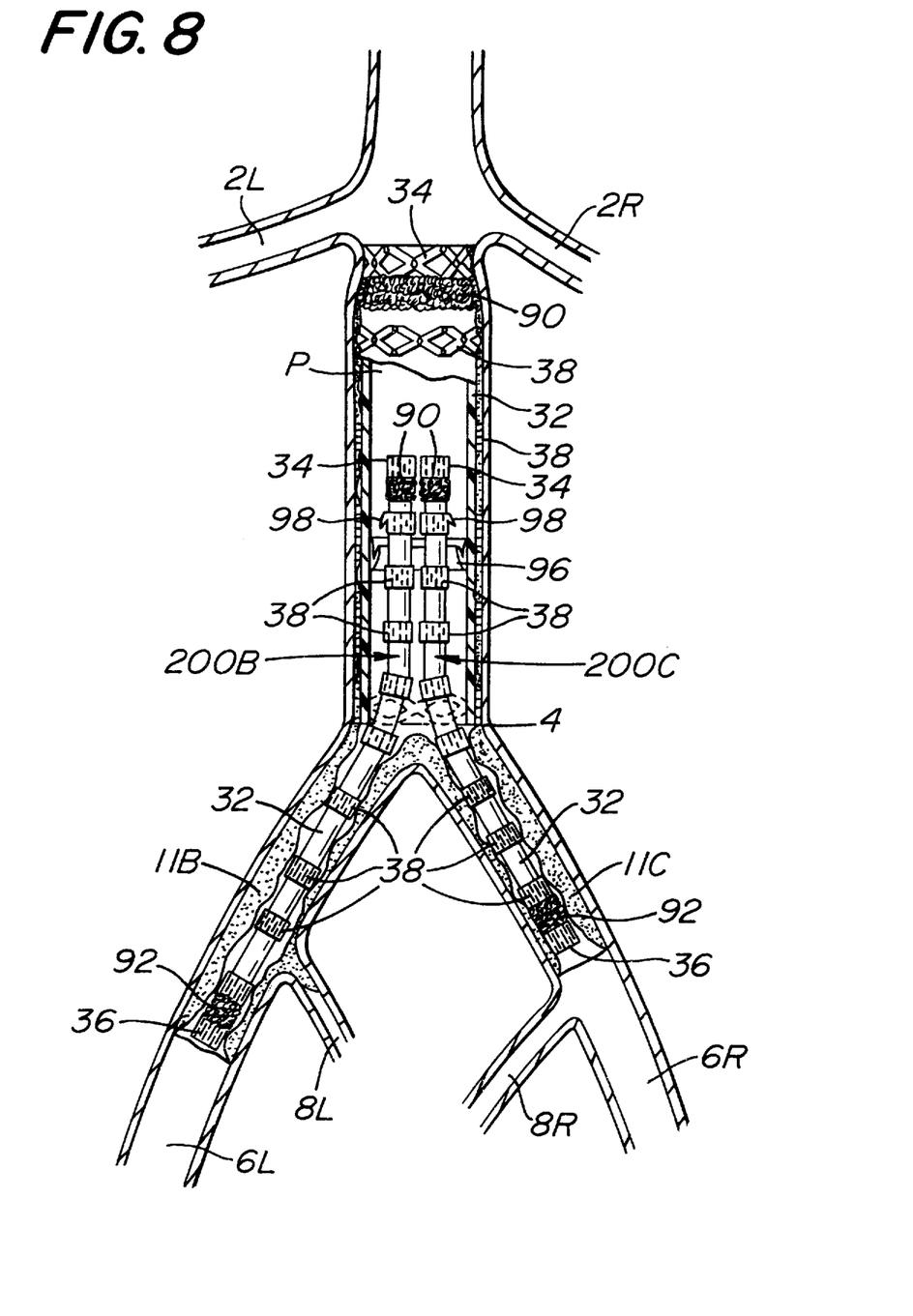
FIG. 8 is a view similar to FIG. 7 but showing the full prosthesis in partial section, and with one portion thereof in its expanded state, and with the other portions of the prosthesis being shown in their compact state.
Figure 9:
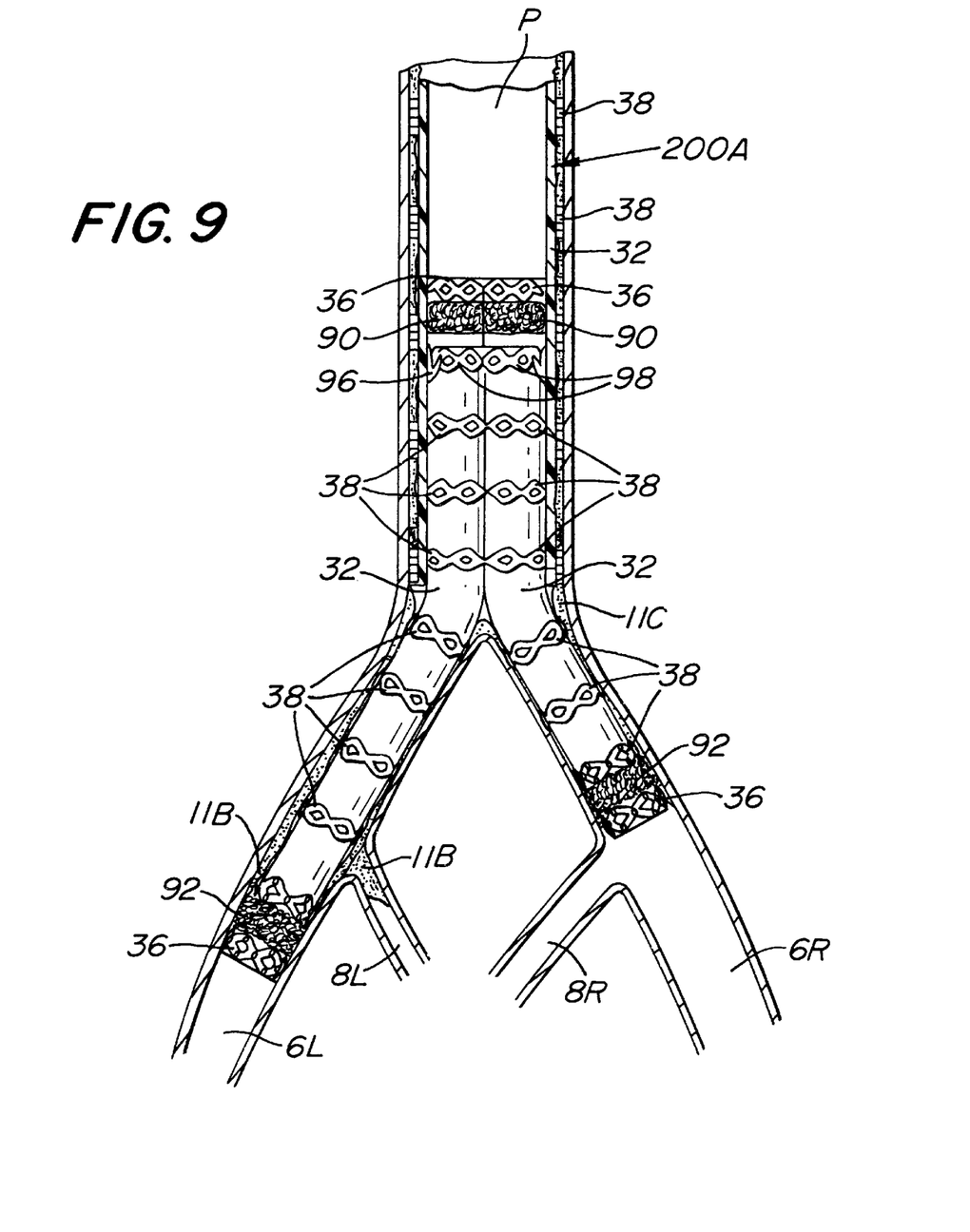
FIG. 9 is an enlarged illustration of a portion of view of FIG. 7 but showing the prosthesis of that figure in its fully expanded operative state.

The prosthesis 200 is arranged for treating occlusive disease also on opposite sides, i.e., upstream and downstream, of an arterial bifurcation. The most commonly anticipated application for the prosthesis 200 is also expected to be for treating a stenosed abdominal aorta and stenosed common iliac arteries adjacent the aorta-iliac bifurcation, i.e., aorto-iliac occlusive disease. When the prosthesis 200 is place in its operative, expanded state (to be described later) it provide for patency of the arterial path. The aorto-iliac application for the prosthesis 200 is shown in FIGS. 7–9 herein.

The prostheses 20 and 20' are each arranged for introduction within a blood vessel, duct or lumen of a living being adjacent a bifurcation, wherein each portion of the vessel, duct, or lumen adjacent the bifurcation has an aneurysm in the wall thereof. Once in position and in its operative state (to be described later) the prosthesis 20/20' serves to prevent further expansion or rupture of the aneurysm, while providing for patency of the vessel, duct, or lumen in which the aneurysm is located. One particularly significant application of the subject invention is the treatment of aneurysmal arterial disease, e.g., the treatment of an aorto-iliac aneurysm like shown in FIG. 1, i.e., an aneurysm 10A in the abdominal aorta and aneurysms 10B and 10C in the contiguous common iliac arteries on each side of the bifurcation. As can be seen therein the aneurysm 10A in the aorta extends for a substantial portion of the abdominal aorta, between the renal arteries 2L and 2R, and the bifurcation 4 of the common iliac arteries 6L and 6R. The aneurysm 10B in the left common iliac 6L extends from the bifurcation 4 to a point slightly distally of the origin of the left internal iliac 8L, while the aneurysm 10C in the right common iliac 6R extends from the bifurcation to a point immediately proximally of the origin of the right internal iliac 8L. As is typical a thrombus 12A is attached to the inner wall of the artery in the aneurysmal space in the aortic aneurysm 10A, a thrombus 12B is attached to the inner wall of the artery in the aneurysmal space in the left iliac aneurysm 10B, and a thrombus 12C is attached to the inner wall of the artery in the aneurysmal space in the right iliac aneurysm 10C.

The prostheses 20 and 20' each include three sections, namely a common section, a left limb section, and a right limb section (all to be described later) which are arranged to be located in the aortic aneurysm, the left iliac aneurysm, and the right iliac aneurysm, respectively, and to be secured together thereat too form an integral unit for permanent location therein. In the interests of brevity only the details of the construction and use of the prosthesis 20 will follow. The details of the differences in construction and operation of the prosthesis 20' will be deferred until later in this specification. Thus, the following description of the construction and operation of the prosthesis 20 also pertains to the prosthesis 20'.

As can be seen clearly in FIG. 1 the prosthesis 20 basically comprises a common section 20A, a left limb section 20B, and a right limb section 20C for location in the aortic aneurysm 10A, the left iliac aneurysm 10B, and the right iliac aneurysm 10C, respectively. As mentioned earlier these sections are arranged to be connected to one another in situ to complete the formation of the prosthesis 20.

The common section 20A is constructed in accordance with the teaching of my aforementioned application Ser. No. 08/562,728, except for internal connection means 96 (to be described later) located within its central passageway. The internal connection means 96 enables the two limb sections 20B and 20C, which as will be described later are disposed within the central passageway of the common section 20A, to be fixedly secured to thereto to complete the assembly of the prosthesis 20.

The common section 20A is arranged for placement within the aneurysmal space in the abdominal aorta by either conventional "cut-down" surgical techniques, or by percutaneous placement. Depending upon the condition of the patient's vascular system, percutaneous placement of the section 20A may be effected by introducing the prosthesis at one puncture situs, e.g., a puncture in the femoral artery, followed by threading or passing the prosthesis through appropriate connecting portions of the vascular system to the situs of the aneurysm 10A. In either type of introduction, e.g., arterial cut-down, or percutaneous, the section 20A is arranged to be initially maintained in a compact or compressed state to facilitate its placement into the aneurysmal space. Once in that space it is arranged to be expanded so that it becomes anchored in place to seal the thrombus 12A between it and the interior wall of the aorta, while providing a passageway through it for blood to flow freely.

The expansion of the prothesis 20 from its compacted state (not shown) to its expanded state shown in FIG. 1 is preferably accomplished by a conventional balloon catheter. However, any other suitable expansion device or instrument, e.g., a mandrel (not shown), may be used for that purpose.

The prosthesis section 20A basically comprises sleeve means 22, outer balloon means 24, anchoring stent means 26, plural intermediate support stent means 28, and sealing means 30. The sleeve means comprises an elongated tubular member 32 having a pair of open ends with a central passageway extending therebetween. The tubular sleeve 32 is formed of a thin and highly flexible material and is pleated, i.e., it includes a plurality of longitudinally extending pleats. Each of the pleats extends the entire length of the sleeve section 20A. The pleated sleeve is normally in a compacted state (not shown), that is each of the pleats overlies and abuts a contiguous portion of an immediately adjacent pleat. The sleeve 32 is arranged to be expanded to a maximum expanded state wherein its pleats open up and form a generally continuous curved, e.g., cylindrical, inner and outer surface. The inner surface forms a passageway P through the prosthesis section through which blood will flow, as will be described later.

The anchoring stent means 26 basically comprises a pair of expandable tubular stents 34 and 36. Each stent is an expandable ring-like, member. One stent 34 is located the end of the prosthesis section 20A adjacent the renal arteries 2L and 2R, while the other stent 36 is located at the other end of the prosthesis adjacent the iliac bifurcation 4. In accordance with a preferred embodiment of this invention the stent 34 is fixedly secured to portions of the outside surface of the sleeve 32 at one end thereof, while the stent 36 is fixedly secured to portions of the outside surface of the sleeve 32 at the opposite end thereof. Each of the stents 34 and 36 includes anchoring means (not shown) constructed in accordance with the teachings of my aforementioned copending U.S. patent application Ser. No. 08/562,728, filed on Nov. 27, 1995, entitled Intravascular Stent With Secure Mounting Means, whose disclosure is also incorporated by reference herein. Those anchoring means basically comprise plural protuberances or projections extending slightly outward from the stents and from the outer surface of the sleeve member. The projections are preferentially oriented so that the force of the fluid, e.g., blood, flowing through the passageway P in prosthesis section 20A is applied to them to cause them to tightly engage the interior of the artery.

The intermediate support stent means 28 comprises a plurality of expandable tubular stents 38, each of which is also an expandable ring-like member. The stents 38 are of slightly smaller outer diameter when expanded than the anchoring stents 34 and 36, and are located at equidistantly spaced positions within the sleeve 32 between the anchoring stents 34 and 36 and are fixedly secured thereto. The stents 38 need not include the anchoring projections.

The anchoring stents 34 and 36 and the intermediate support stents 38 serve as a means for holding or retaining the sleeve 32 in any desired expanded state, i.e., from the compact or compressed state, to the fully expanded state like shown in FIG. 1. Each of the stents 34, 36, and 38 basically comprises a plurality of pivotally interconnected links or struts. The links are arranged to pivot outward with respect to each other so that the angle therebetween increases, yet are precluded from pivoting backward toward each other. Thus, the stents can be expanded outward radially, but are resistant to being collapsed once expanded.

The outer balloon means 24 basically comprises an annular member having a cylindrical inner wall 70, a generally cylindrical outer wall 72, and interconnecting end wall portions (not shown) defining a hollow space 78 therebetween. The balloon 24 is an integral unit, preferably formed of a very flexible material, such as that typically used in conventional balloon catheters. The inner surface of the inner wall 70 of the balloon is fixedly secured by any suitable means, e.g., an adhesive (not shown), to the outer surface of the sleeve 32 and the outer surface of the intermediate support stents 38 between the pair of anchoring stents 34 and 36. An self-sealing port (not shown) is provided in the balloon for communication with a tube or conduit (not shown) extending from outside the body of the patient. The conduit is arranged to carry a fluid, e.g., a gel or saline solution therethrough for introduction through the port into the interior 78 of the balloon to inflate the balloon. Preferably the balloon's interior 78 is filled sufficiently to cause the outer wall of the balloon to extend outward to completely fill the aneurysmal space longitudinally, but only to partially fill the aneurysmal space transversely so that an excess force is not produced radially which could dislodge the aneurysm thrombus. This action causes respective portions of the outer surface of the outer wall 72 to engage the surface of the thrombus 12A and the inner surface of the abdominal aorta on the proximal and distal sides of the thrombus. Accordingly, the thrombus is trapped between the outer wall of the balloon and the inside surface of the artery wall. Once the balloon has been expanded sufficiently to seal the aneurysmal space, as just described, the conduit can be removed, whereupon the self-sealing port closes to trap the fluid within the balloon, thereby keeping the balloon inflated. The inflation of the balloon with the fluid effects the stiffening of the prosthesis section 20A, thereby rendering it resistant to migration.

In order to seal the aneurysmal space within the aneurysm 10A, i.e., to prevent any blood from flowing into the aneurysmal space between the outer surface of the outer balloon and the inner surface of the artery at the proximal end of prosthesis section 20A, and for precluding the egress of any emboli out of that aneurysmal space 12A at the distal end of the prosthesis section, the heretofore identified sealing means 30 are provided. That means basically comprises a pair of sealing rings 90 and 92 located adjacent the proximal and distal ends, respectively, of the prosthesis section 20A. Each of the sealing rings is formed of any suitable material, e.g., a mesh of loosely organized or loosely disorganized fibers which are thrombogenic and fibrogenic, to promote hemostasis between the prosthesis section and the arterial wall. Being fibrogenic, the sealing rings also promote or stimulate the incorporation of the ends of the prosthesis section by fibrosis to the interior of the aorta wall. Each sealing ring is also expandable so that when the prosthesis is expanded, each sealing ring expands with it.

When the prosthesis's common section 20A is in place and expanded to its operative state like shown in FIG. 1, the sealing rings 90 and 92 are interposed between the outer surface of the section and the inner wall of the abdominal aorta on opposite sides of the aneurysm 10A, i.e., proximally and distally. This action effectively blocks the ingress of blood into the aneurysmal space and the egress of emboli therefrom.

Figure 6:
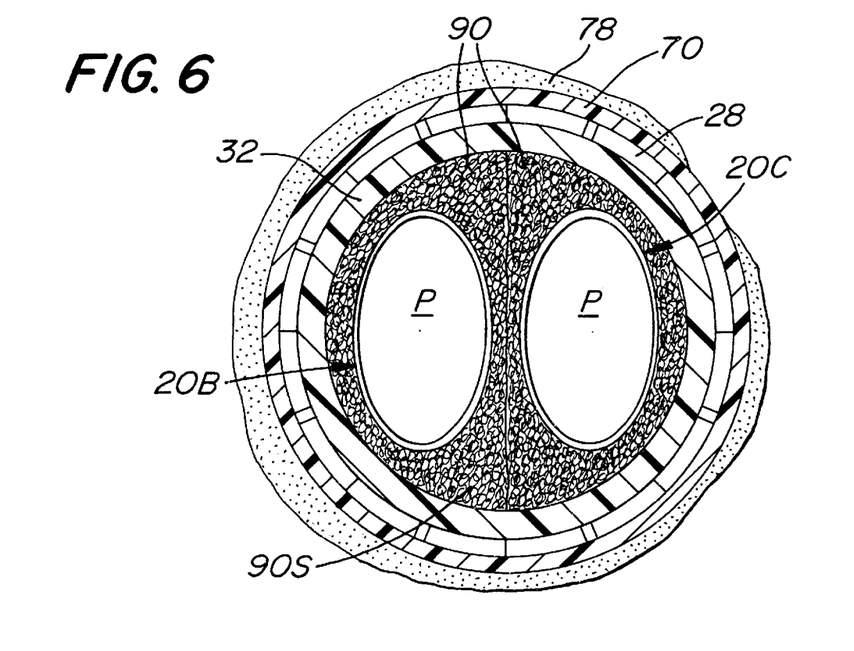
FIG. 6 is an enlarged sectional view taken along line 6—6 of FIG. 2.

The details of the internal connection means 96 for securing the limb sections 20B and 20C to the common section 20A will be described later. Suffice it for now to state that such means is mounted within the passageway in the sleeve 32 of section 20A at an intermediate location therealong as shown in FIG. 1. The connection means 96 is arranged for engagement by external connecting means 98 on the proximal end of each of the prosthesis' limb sections 20B and 20C to effect the permanent connection therebetween to complete the prosthesis. The construction of the two limb sections 20B and 20C will also be described shortly. Suffice it for now to state that each limb section 20B and 20C comprises an elongated, expandable, tubular sleeve having a proximal end and a distal end and a passageway P extending therebetween. Each limb section is arranged to be placed within its respective aneurysm in its compact state so that its proximal end extends proximally of the bifurcation and within the passageway of the expanded common section 20A. As mentioned above, each of the prosthesis' limb sections 20B and 20C includes external connection means 98 at its proximal end which is arranged to cooperate with the internal connection means 96 of the common section 20A when the limb sections are expanded to their operative state to fixedly secure each of the limb sections to the common section. A sealing ring 90, similar to the proximally located sealing ring 90 on the common section 20A, is provided on the proximal end of each of the limb sections 20B and 20C. These sealing rings 90 cooperate with each other to produce a hemostatic seal between the outer surface of the proximal ends of the limb sections 20B and 20C and the inner surface of the common section 20A when the limb sections 20B and 20C are expanded and connected to the common section 20A. Thus, as can be seen in FIG. 6 when the prosthesis sections 20B and 20C are expanded, their proximally located sealing rings 90 are compressed against the interior of the common graft section 20A and against each other to form a seal 90S filling the interstitial space or interface between the sections 20B and 20C. In particular, the hemostatic seal 90S is formed by blood infiltrating the loose fibers of the mesh rings 90, whereupon hemostasis occurs rapidly, thereby preventing further leakage of blood out of the seal 90S. When the two limb sections are expanded, their respective proximal ends are deformed from their normally round shape to a somewhat oval shape due to their confinement within the common section 20A and the compression of the sealing rings 90. This sealing action ensures that the passageways P through the sections 20A, 20B, and 20C are in fluid communication with one another, so that no blood will leak out the interface seal 90S between these sections, i.e., all of the blood flowing through the passageway P in common section 20A will enter the passageway P in the two limb sections for passage therethrough. A sealing ring 92, like that of common section 20A, is also provided on the distal end of each of the limb sections 20B and 20C to effect a seal between it and its contiguous artery wall, in the same manner as described with respect to common section 20A.

The expandable limb sections 20B and 20C can be constructed either similarly to the common section 20A or similarly to the prosthesis of my aforementioned patent, or other suitable expandable construction, depending upon the longitudinal extent of the aneurysm within the iliac artery in which the limb section is to be disposed. In this regard if the aneurysm in the iliac artery extends distally of the origin of the internal iliac artery, the limb section is preferably constructed similarly to the section 20A (and the teachings of my aforementioned copending patent applications) so that upon expansion of the iliac limb section, its external balloon occludes the internal iliac artery. This action thus deprives the iliac aneurysm of a potential source of blood, i.e., blood from the internal iliac, which could result in the growth and possible rupture of the iliac aneurysm. As will be appreciated by those skilled in the art the occlusion of the internal iliac by the expanded limb section should not prove to be a major problem since blood to the affected leg will likely be supplied by various collateral vessels. Thus, the section 20B is constructed similarly to section 20A, except that section 20B does not include the heretofore mentioned internal connection means 96, but does include the external connection means 98 at its proximal end. In the interests of brevity, the common components of the sections 20A and 20B will be given the same reference numbers, and their construction and operation will not be reiterated.

If the aneurysm in the iliac artery does not extend to the origin of the internal iliac artery, the limb section can be of a simpler construction than section 20B. In this regard the limb section of the prosthesis 20 can constructed similarly to the teachings of my aforementioned patent, or any other suitable expandable sleeve. In the embodiment shown herein the limb section 20C is constructed in accordance with the teachings of that patent, except for the inclusion of external connection means 98 located at the proximal end of the section 20C and sealing rings 90 and 92 located at the proximal and distal ends, respectively, of the limb section 20C. Thus, the limb section 20C basically comprises an elongated tubular member or sleeve 32, like that of sections 20A and 20B, having a pair of open ends with a central passageway extending therebetween. Mounted on the exterior of the sleeve 32 at substantially equidistantly locations are plural expandable tubular stents 34, 36, and 38. The stents 34 and 36 located adjacent the ends of the sleeve 32 include the heretofore identified locking projections or protuberances, while the intermediately located stents may be constructed like the stents 38 of sections 20A and 20B, or may be constructed like the stents 34 and 36. In any case the stents of the limb section 20C, like the stents on the sections 20A and 20B, serve as the means for holding or retaining the sleeve 32 in any desired expanded state, i.e., from the compact or compressed state of FIG. 1, to the fully expanded state like shown in FIG. 2.

The following constitutes the methodology for placing the prosthesis's various sections in place and assembling them. The common section 20A in its compact state is crimped over an introducing instrument, e.g., a conventional balloon catheter like that shown by the phantom lines designated BC in FIG. 7, so that the instrument extends through the compacted passageway in the sleeve 32. The prosthesis is then ready to be introduced into the aneurysm 10A through an introducing sheath (not shown), usually at some distance from the aneurysm, e.g., a percutaneous puncture in the femoral artery. Prior to such introduction, a balloon catheter (not shown) is introduced into one of the iliac arteries via a percutaneous puncture in the associated femoral artery. The balloon catheter is located so that the balloon at its distal end is located below the aneurysm in the redundant loop of the iliac artery, and is expanded to occlude that artery below the aneurysm. This action prevents any thrombus from entering that artery during the deployment of the prosthesis of this invention. Once the occluding balloon catheter is in place and operating, a conventional guide wire is then threaded into the abdominal aorta through the other iliac artery from a percutaneous puncture site in the associated femoral artery. If desired, a thicker, stiffer guide wire can be threaded over the first guide wire to help straighten the redundant loop of the iliac artery. The introducer sheath is then slid over the guide wire to its desired position within the abdominal aorta.

Preferably the introducer sheath is an expandable member having a centering balloon at its distal end. Thus, once the sheath is in position the balloon at the end of thereof is inflated to center the sheath within the artery. The sheath can then expanded radially outward along its entire length by any suitable means (e.g., a balloon catheter, a mandrel, etc.) to provide a relatively large diameter lumen therethrough. The large lumen facilitates the passing of the prosthesis 20 of this invention and it associated introducing balloon catheter BC through the sheath to the desired situs within that abdominal artery. The expansion of the sheath also has the effect of further linearizing or straightening the path from the femoral puncture site to the situs of the aortic aneurysm, e.g., straightening the redundant loop of the external iliac artery.

Once the prosthesis on its deployment balloon is in the desired position within the abdominal aorta, the centering balloon on the sheath is then collapsed and the sheath withdrawn to a position immediately adjacent the bifurcation with the associated iliac artery. This action effectively uncovers ("extrudes") the common section 20A of the prosthesis in the abdominal aorta. The centering balloon and its sheath are then re-expanded in the retracted position to hold the sheath centered in the associated iliac.

The sleeve 32 and the anchoring stents 34 and 36 and intermediate support stents 38 of the common section 20A are then expanded as a unit by the balloon catheter BC to a partially expanded state, i.e., a state slightly smaller than the prosthesis' fully expanded state shown in FIG. 1. The balloon catheter (not shown in FIG. 1), is left in place within the partially expanded prosthesis section 20A. The outer balloon 24 is then inflated by introducing the inflation fluid into it. The partially expanded stents 34, 36 and 38 prevent the radially inward collapse of the inner wall 70 of the balloon 24 during and after inflation.

After the outer balloon 24 is filled sufficiently to create the desired rigidity, and a good seal at both ends, the filling conduit is removed, thereby causing the self-sealing port in the balloon to seal shut. This action entraps the inflation fluid 84 within the outer balloon to maintain its rigidity. The introducing balloon catheter is then inflated to complete the expansion of the sleeve member 32 and associated stents 34, 36 and 38 (i.e., to expand them to their fully expanded state shown in FIG. 1). This action causes the outer surface of the outer wall 72 of the balloon 24 to engage and compress the thrombus 12A within the aneurysmal space, while the anchoring stents move into very close proximity to the contiguous inner surfaces of the arterial wall so that their locking protuberances tightly engage those surfaces. The introducing balloon catheter is then withdrawn from the passageway through the sleeve member by deflating its balloon and then pulling it out of the prosthesis section.

Once the common section 20A is in place and expanded to its operative state, as described above, the expandable sheath in the iliac artery is advanced into the interior of the common section 20A until is distal end is adjacent the connector ring 96 of the common section. The occluding balloon (not shown) in the opposite iliac artery is then removed and another expandable sheath is introduced therein until its end is located immediately beside the end of the first expandable sheath adjacent the connector ring 96 in the common section 20A.

The iliac limb sections 20B and 20C are collapsed and introduced, via the expanded sheaths, through their respective iliac aneurysms to the interior of the expanded common section 20A. In particular, each limb section is advanced through its associated expanded sheath until its distal end bearing the connector means 98 is immediately above the internal connector ring 96. The expandable sheaths are preferably withdrawn somewhat so that they are still located within their associated iliac, but below the prosthesis' limb sections. This action ensures that any emboli produced during the expansion and locking of the limb sections to each other and to the common section (as will be described immediately hereinafter) will be collected thereby and can be flushed out of the patient's body. It should be noted that the expandable sheaths are not shown in FIG. 1 in the interests of drawing simplicity.

The limb sections are then expanded and pulled distally with respect to the common section 20A so that the external connector means 98 of each is immediately adjacent the internal connection means 96 of the common section 20A. Continued pulling of the limb sections causes the external connecting means 96 to engage the internal connection means to secure the limb sections 20B and 20C to the common section 20A. The expansion of both of the limb sections is preferably done simultaneously using respective balloon catheters (like balloon catheter BC) in a similar manner to the expansion of common section 20A, so that each limb section is in the state shown in FIGS. 2–4 and 6. This expansion enables anchoring projections (to be described later) of the external connector means 96 to be aligned for receipt within recesses (also to be described later) of the internal connecting means to permanently secure or lock the sections to one another.

As mentioned earlier, the expansion of the limb sections also forms the hemostatic seal 90S at the interface of those limb sections within the common section and 20C also seals the sections in their respective iliac arteries.

The expandable sheaths are then collapsed and withdrawn fully out of the patient's body.

Figure 2:
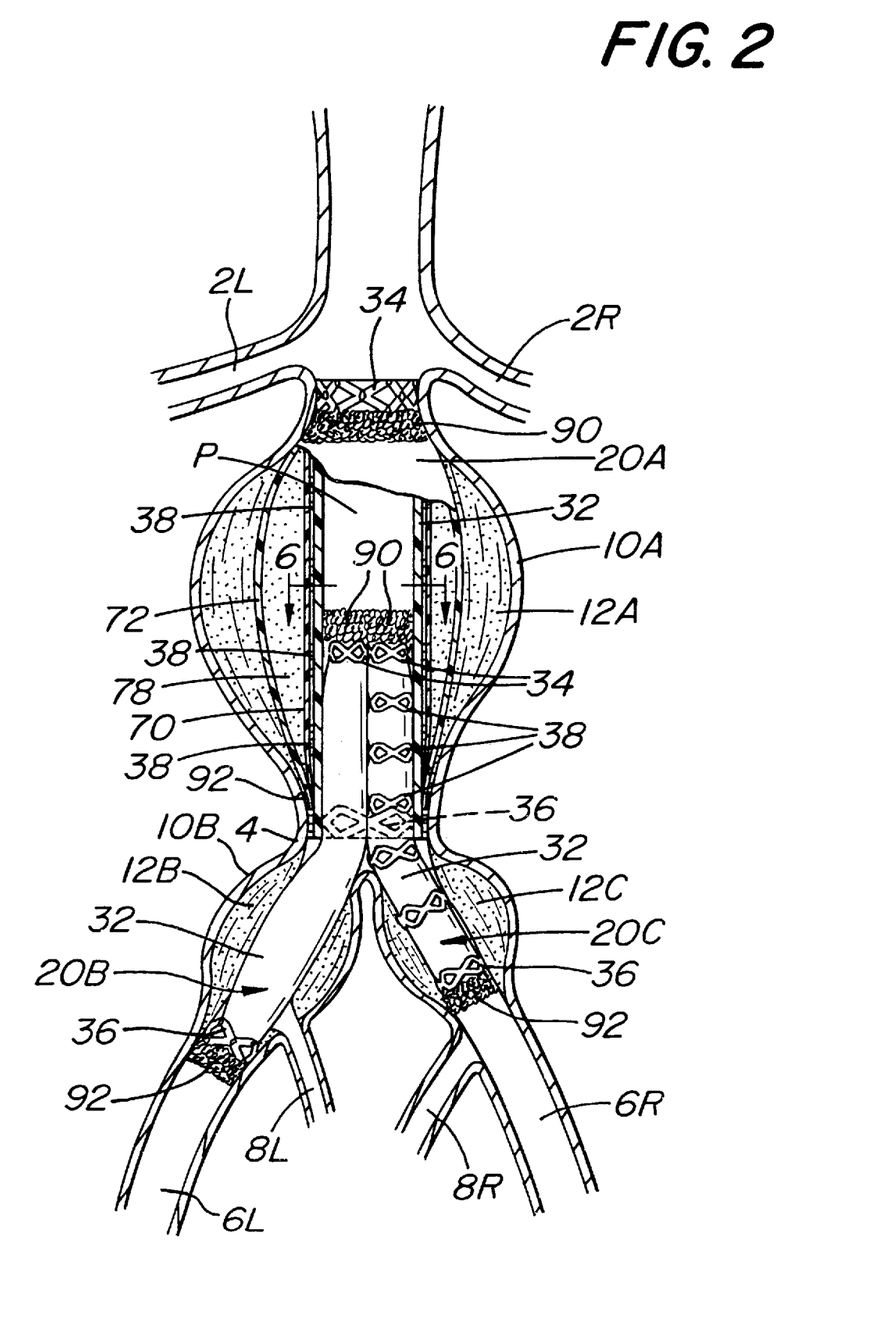
FIG. 2 is a view similar to FIG. 1 but showing the prosthesis of FIG. 1 in its fully expanded, operative state.

As should be appreciated by those skilled in the art, once the prosthesis 20 is in place and its sections 20A, 20B, and 20C expanded and connected together as shown in FIG. 2, blood is able to flow through the communicating passageways P in the prosthesis 20 in the normal direction, with the proximally located sealing member 90 on the section 20A preventing any ingress of blood into the aneurysmal space 12A between the outer wall of the prosthesis section 20A and the inner surface of the artery at the proximal end of the aneurysm 10A. The distally located sealing ring 92 on section 20A prevents the egress of any emboli from the aortic aneurysmal space at the distal end of thereof. The blood flowing through the passageway P in the prosthesis section 20A applies a force to the protuberances (not shown) on its stents to cause them to more tightly engage, e.g., burrow slightly, into the arterial wall, to thereby lock the prosthesis section in place against migration. Moreover the sealing rings at the distal ends of the limb sections 20B and 20C prevent the egress of any emboli from their respective aneurysmal spaces 12B and 12C at the distal end of each of those limb sections.

In some applications additional sealing means, e.g., a sealing mesh covering 100 (FIG. 10) extending over substantially the entire exterior surface of one or more of the prosthesis' sections may be desirable, e.g., to ensure that a complete seal is formed between the prosthesis and the interior of the artery wall. The limb sections 20B and 20C, may also include the covering 100 to assist in sealing and fibrosis to the arterial wall. The covering 100, like the sealing rings 90 and 92, is preferably formed of a mesh of either loosely organized or loosely disorganized fibers in order to expedite and promote hemostasis. In addition, the fibers are preferably formed of a material, e.g., dacron, which is thrombogenic and fibrogenic. Thus, when the prosthesis section including the covering 100 is located within its aneurysm and fully expanded to the operative state, its covering 100 will engage the inner surface of the artery wall to seal it as described earlier, while the fibrillar fibers of the covering 100 are compacted into the aneurysmal thrombus to intermingle with the thrombus and thereby lock the prosthesis in place. Moreover, since the mesh covering is thrombogenic and fibrogenic it stimulates the incorporation of the prosthesis section by fibrosis to the artery wall, thus ensuring a complete and permanent seal. Thus, the prosthesis section 20A prevents further aneurysmal expansion and rupture by also strengthening the artery wall due to fibrosis. Moreover, if the prosthesis section which is provided with the covering mesh is of the balloon type, like the common section 20A, or the limb section 20B, the mesh covering 100 will effect the occlusion of collateral branches to the artery at which the prosthesis section is located, thereby preventing further aneurysm growth. For example, a covering 100 on the common section 20A should result in the occlusion inferior mesenteric artery and the lumbar arteries, thereby preventing a source of further aortic aneurysm growth and its attendant risk of rupture.

In FIG. 10 there is shown a prosthesis 20' including the alternative sealing covering 100. It must be pointed out at this juncture that the prosthesis 20' is in all respects the same as the prosthesis embodiment 20 described heretofore except for the sealing covering. Thus, as can be seen the section 20A of prosthesis 20' includes a sealing covering 100 disposed over and secured to the outer surface of the outer wall 72 of the balloon 24. The proximal end (cuff) portion of the prosthesis section 20A of prosthesis 20' is preferably devoid of the covering mesh 100 in order to prevent the protrusion of the mesh into the origins of the renal arteries above the prosthesis.

Figure 3:
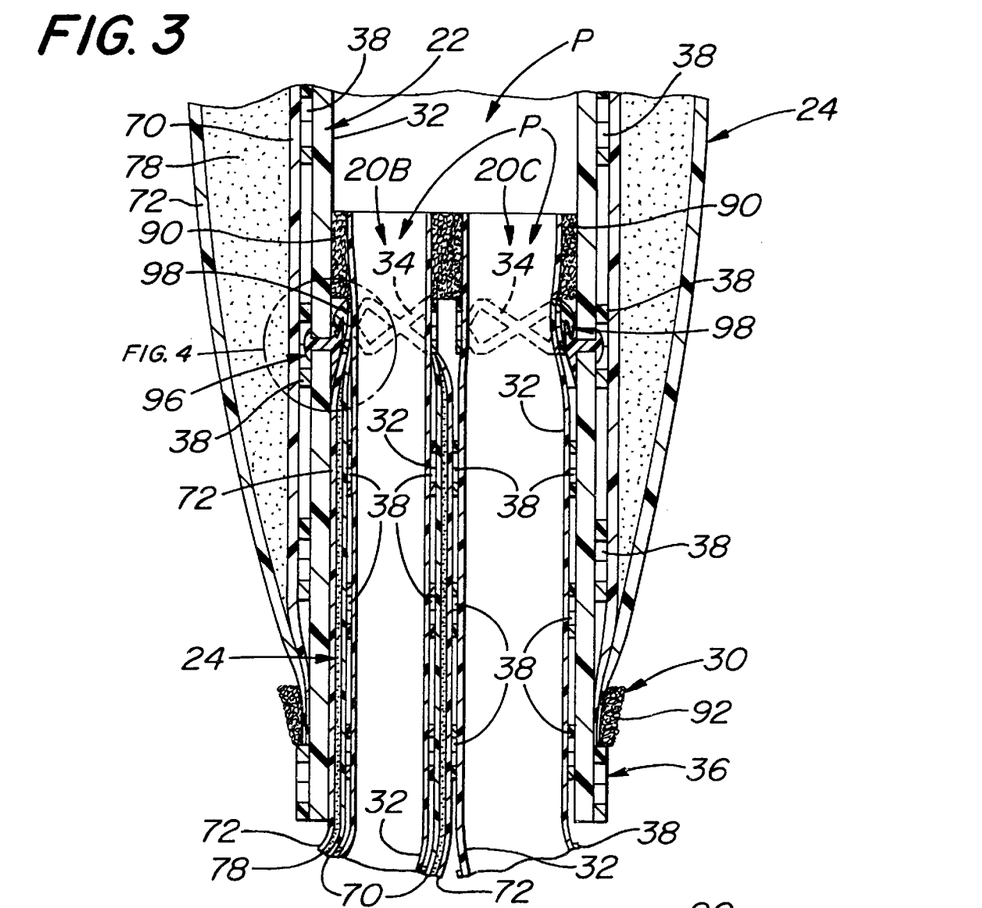
FIG. 3 is an enlarged longitudinal sectional view of the portion of the prosthesis of FIG. 1 which is at adjacent the aorta-iliac bifurcation.
Figure 4:
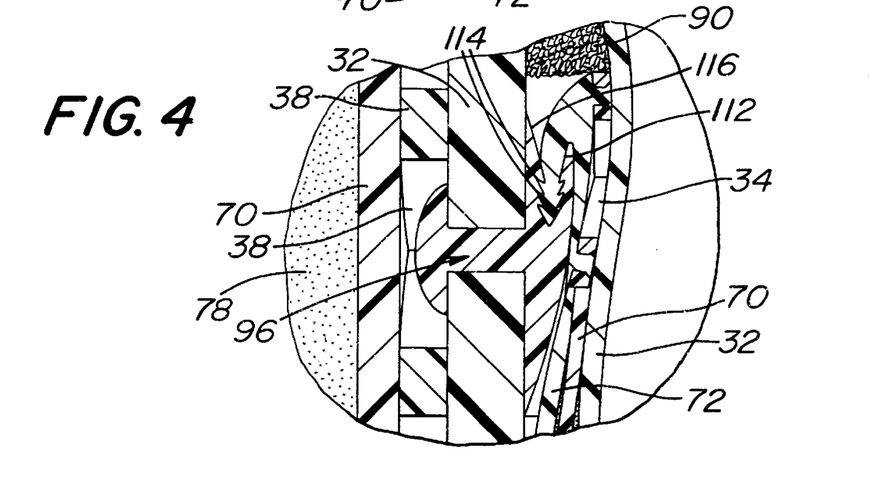
FIG. 4 is an enlarged sectional view of the portion of the prosthesis bounded by the circle bearing the legend "FIG. 4" in FIG. 3.

Referring now to FIGS. 3 and 4, the details of the internal connecting means 96 of the common section 20A, and the external connecting means 98 of the limb sections 20B and 20C will now be discussed. The internal connecting means 96 basically comprises an expandable ring 110 (FIG. 5) attached to the interior surface of the expandable sleeve 32 of the prosthesis section 20A. The ring 110 is sized so that it is of substantially circular shape when the sleeve 32 is in its fully expanded state shown in FIGS. 1, 2, 5 and 6. The ring includes plural recess portions 112 at equidistantly spaced locations along the inner periphery of the sleeve 32 when the sleeve is in the fully expanded state (see FIG. 5). It should be noted at this juncture that the recess portions 112 can consist of a continuous annular recess extending about the inner periphery of the sleeve 32 (i.e., the ring be continuous, as shown) or may be separate recesses formed in movable discrete sections of a ring, and which sections move into general alignment with one another when the sleeve 32 fully expanded. In either case each recess portion 112 is of a generally V-shaped cross section, having plural undercut notches 114 therein, as shown in FIG. 4. Respective inclined cam surfaces 116 extend from the inner surface of the sleeve 32 to the entrance to each recess portion 112. The securement of the ring 110 having the recess portions 112 therein to the sleeve 32 is accomplished via plural rivet portions 118 extending through the thickness of the sleeve.

Figure 5:
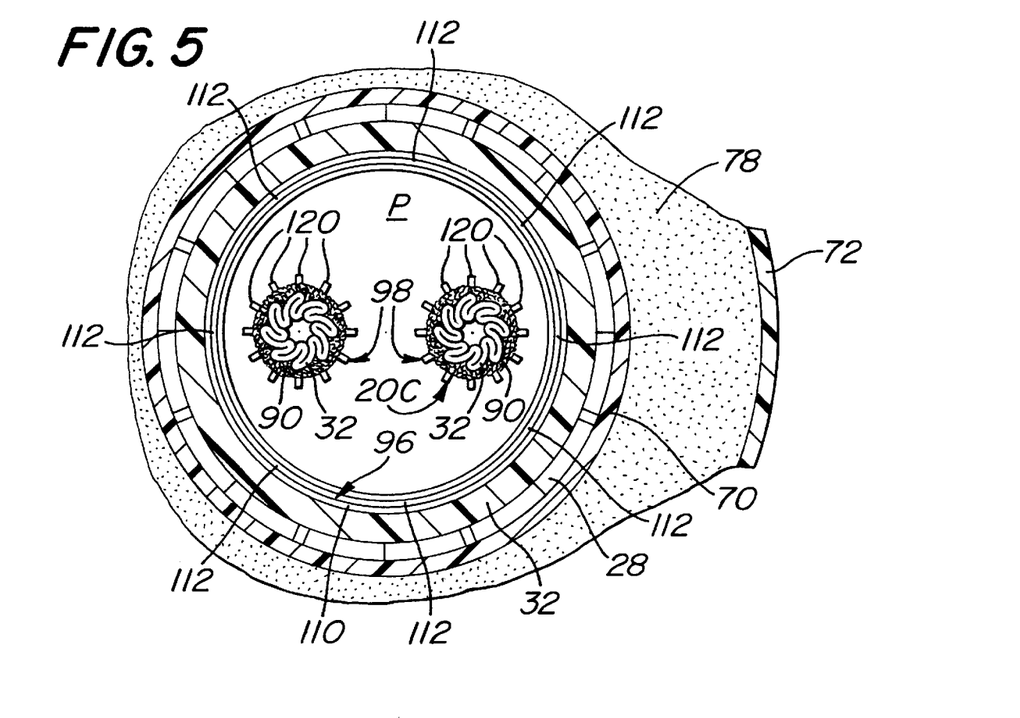
FIG. 5 is an enlarged sectional view taken along line 5—5 of FIG. 1.

Plural of the recess portions 112 are arranged to receive therein male anchor projections 120. The anchor projections 120 form a portion of the external connecting means 98 of each of the limb sections 20B and 20C. Thus, as can be seen in FIG. 5 each external connecting means 98 thus comprises a plurality of male anchor projections 120 fixedly secured to the sleeve 32 of the limb section and extending outward from the periphery thereof. Each anchor projection 120 of each limb section is shaped to be received in and mate with whichever recess portion 112 of the connector ring 110 is disposed contiguous with it when the limb section is expanded to the state shown in FIG. 6. In fact, as will be described shortly, when an anchor projection is received within an associated recess portion it is locked in place and resistant to disconnection.

The connection of the limb sections 20B and 20C to the common section 20A via the connector means 96 and 98 is as follows. As mentioned earlier, the limb sections are initially positioned so that the proximal end of each is located proximally of the internal connecting means, i.e., the ring 110, as shown in FIG. 1. The limb sections are then expanded and pulled distally with respect to the common section 20A so that some of their radially outwardly extending anchor projections 120 are disposed immediately adjacent the ring 110. Continued pulling on the limb sections in the distal direction causes those projecting anchors which are disposed immediately adjacent the ring to ride or slide up the cam surfaces 116, whereupon they enter and lock into the notched V-shaped recesses. This action effectively permanently locks the limb sections 20B and 20C to the common section 20A.

Referring now to FIGS. 7–9 there is shown at 200 an expandable, intraluminal prosthesis constructed in accordance with this invention for treating occlusive disease at a bifurcation of a vessel, duct, or lumen, e.g., for treating aorto-iliac occlusive disease. For that application, the prostheses 200 is arranged for introduction within an artery adjacent the aorto-iliac bifurcation, wherein each portion of the artery adjacent the bifurcation is partially occluded or stenosed. Once in position and in its operative state (to be described later) the prosthesis 200 renders the arterial aorto-iliac patent. In FIG. 7 there is shown an stenotic lesion 11A in the abdominal aorta and similar lesions 11B and 11C in the contiguous common iliac arteries on each side of the aorto-iliac bifurcation 4. As can be seen therein the lesion 11A in the aorta extends for a substantial portion of the abdominal aorta, between the renal arteries 2L and 2R, and the bifurcation 4 of the common iliac arteries 6L and 6R. The lesion 11B in the left common iliac 6L extends from the bifurcation 4 to a point slightly distally of the origin of the left internal iliac 8L, while the lesion 11C in the right common iliac 6R extends from the bifurcation to a point immediately proximally of the origin of the right internal iliac 8L.

Like the prostheses 20 and 20' described earlier, the prosthesis 200 includes three sections, namely, a common section 200A, a left limb section 200B (FIG. 8), and a right limb section 200C which are arranged to be located in the abdominal aorta, the left iliac, and the right iliac, respectively, and once in position to be secured together thereat to form an integral unit for permanent residence therein. The common section 200A is constructed in accordance with the teachings of my aforementioned patent and is similar in construction to limb section 20C described heretofore. However, the common section 200A includes internal connection means 96, like that of section 20A, mounted within its sleeve 32 at an intermediate point therealong to enable the limb sections 200B and 200C to be connected thereto in the same manner as described earlier with respect to sections 20B and 20C. In addition, the common section 200A includes sealing rings 90 and 92 at its proximal and distal ends respectively. The limb sections 200B and 200C are of identical construction to each other, except for their length, and are similar to limb section 20C. In the interest of brevity the common components of the various sections 200A, 200B, and 200C of prosthesis 200 will be given the same reference numbers as the common components of the various sections 20A, 20B, and 20C, and a description of their structure and operation will not be reiterated.

The following constitutes the methodology for placing the occlusive disease prosthesis's various sections in place and assembling them. An expandable sheath like that described with respect to the aneurysmal disease prosthesis 20A is introduced into position within the artery. The common section 200A in its compact state is crimped over an introducing instrument, e.g., a conventional balloon catheter BC (shown by the phantom lines in FIG. 7), so that the instrument extends through the compacted passageway in the sleeve 32. The prosthesis is then introduced through the expanded, centered, sheath into the lesion 11A in the abdominal aorta to the position shown in FIG. 7 (the sheath not being shown in the interest of drawing simplicity). The sleeve 32 and the anchoring stents 34 and 36 and intermediate support stents 38 are then expanded by the balloon catheter BC as a unit to a fully expanded state shown in FIG. 8 in a similar manner as that described with reference to common section 20A of prosthesis 20. The expanded stents 34, 36 and 38 prevent the radially inward collapse of the sleeve 32. The expansion of the sleeve causes its outer surface to engage and compress the lesion 11A within the abdominal aorta, while the anchoring stents move into very close engagement with the lesion and/or the contiguous inner surfaces of the aorta wall so that their locking protuberances (not shown) tightly engage the lesion and/or arterial surface. The introducing balloon catheter BC is then withdrawn from the passageway P through the sleeve 32 by deflating its balloon and then pulling it out of the prosthesis section 200A.

Once the common section 200A is in place and expanded to its operative state as shown in FIG. 8, as described above, each of the iliac limb sections 200B and 200C is collapsed and introduced into its respective iliac in a similar manner to the placement of the common section 200A. As can be seen in FIG. 2 the limb sections are initially positioned so that the proximal end of each is located proximally of the internal connection means 96. The limb sections are then expanded and pulled distally with respect to the common section 200A to the position shown in FIG. 9 so that the anchor projections of the external connector means 98 of each engages the recesses in the internal connection means 96 of the common section 200A as described earlier to permanently secure the sections 20B and 20C to the common section 20A. The expansion of the sections 200B and 200C also seals those sections within their associated iliac arteries.

As should be appreciated by those skilled in the art once the prosthesis 200 is in place and its sections 200A, 200B, and 200C expanded and connected together as shown in FIG. 9, blood is able to flow more freely through the prosthesis 200 than had occurred theretofore.

Without further elaboration the foregoing will so fully illustrate my invention that others may, by applying current or future knowledge, adopt the same for use under various conditions of service.

I claim:

1. A prosthesis for the treatment of aneurysmal disease adjacent a bifurcation in a vessel, duct, or lumen of a living being, a portion of the vessel, duct or lumen proximal to the bifurcation having an aneurysm in the wall thereof defining an aneurysmal space, the bifurcation comprising a pair of branches of the vessel, duct, or lumen, with each of the branches having an aneurysm in the wall thereof defining an aneurysmal space, said prosthesis being arranged for introduction into the body of a living being with a common portion located in the portion of the vessel, duct, or lumen at the site of an aneurysmal space, and a pair of portions located within respective ones of the branches of the bifurcation at the sites of the aneurysmal spaces in the branches, said prosthesis comprising a common sleeve, a pair of limb sleeves, sealing means, sleeve connecting means, anchoring means, and outer balloon means;

(a) said common sleeve comprising an elongated tube having an open upper end and an open lower end defining a passageway therebetween for conveying a body fluid therethrough, said common sleeve being arranged to be fixedly secured to the interior of the vessel, duct, or lumen by said anchoring means, and with said upper and lower ends of said common sleeve being sealed to portions of the vessel, duct, or lumen on respective sides of the aneurysm therein by portions of said sealing means, (b) said outer balloon means being coupled to and dispose about said common sleeve and arranged to be filled with a filling material to fill the aneurysmal space within the vessel, duct, or lumen, and to preclude the egress of body material from between the outer balloon means and the interior of the vessel, duct, or lumen at the situs of the aneurysm, (c) said limb sleeves being arranged to be located within respective ones of the branches of the bifurcation, with each of said limb sleeves comprising an elongated tube having an open upper end and an open lower end defining a passageway therebetween for conveying the fluid therethrough, said upper open ends of each of said limb sleeves being arranged to be fixedly secured to said common sleeve by said sleeve securement means at a location within said open bottom end of said common sleeve, whereupon said passageway in said common sleeve is in fluid communication with said passageways in said limb sleeves, and with portions of said sealing means being interposed between said common sleeve and said limb sleeves adjacent said joint to preclude the egress of the fluid from said joint.

2. The prosthesis of claim 1 wherein said common sleeve is expandable to an expanded state when in position, and is held in said expanded state by at least one stent.

3. The prosthesis of claim 2 wherein each of said limb sleeves is expandable to an expanded state when in position, and is held in said expanded state by at least one stent.

4. The prosthesis of claim 1 wherein each of said limb sleeves is expandable to an expanded state when in position, and is held in said expanded state by at least one stent.

5. The prosthesis of claim 1 wherein said anchoring means comprises at least one expandable stent.

6. The prosthesis of claim 1 wherein said sealing means comprises mesh material located adjacent the upper and lower ends of said common sleeve to seal said upper and lower ends of said common sleeve to the portions of the vessel, duct, or lumen on respective sides of the aneurysm.

7. The prosthesis of claim 6 wherein said sealing means comprises mesh material interposed between said common sleeve and said limb sleeves adjacent said joint to preclude the egress of the fluid from said joint.

8. The prosthesis of claim 1 wherein said sealing means comprises mesh material interposed between said common sleeve and said limb sleeves adjacent said joint to preclude the egress of the fluid from said joint.

9. The prosthesis of claim 1 wherein said anchoring means comprise plural projections arranged for engagement with the interior of the wall of the vessel, duct, or lumen.

10. The prosthesis of claim 1 wherein said sleeve securement means comprises a first connector member fixedly secured to said common sleeve and a pair of connector members, one of said pair of connector members being fixedly secured to one of said limb sleeves, and the other of said pair of connector members being fixedly secured to the other of said limb sleeves, said first connector member being arranged to be connected to each of said pair of connector members.

11. The prosthesis of claim 10 wherein said first connector member is arranged to matingly engage each of said pair of connector members.

12. The prosthesis of claim 1 wherein at least one said limb sleeves additionally comprises an outer balloon means disposed thereabout and arranged to be filled with a filling material to preclude the egress of body material from between the outer balloon means and the interior of the branch of the vessel, duct, or lumen at the situs of the aneurysm therein.

13. The prosthesis of claim 1 wherein said prosthesis comprises a flexible material to enable said prosthesis to bend longitudinally for ready placement within a curved vessel, duct, or lumen.

* * * * *